US00PP19528P2

(12) United States Plant Patent
Bradford

(10) Patent No.: US PP19,528 P2
(45) Date of Patent: Dec. 2, 2008

(54) INTERSPECIFIC TREE NAMED 'PLUMSWEET X'

(50) Latin Name: ***Prunus* sp.**
Varietal Denomination: Plumsweet X

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,891

(22) Filed: Nov. 26, 2007

(51) Int. Cl.
*A01H 5/00* (2006.01)

(52) U.S. Cl. ..... Plt./180

(58) Field of Classification Search ..... Plt./180
See application file for complete search history.

(56) References Cited

U.S. PATENT DOCUMENTS

| | | | |
|---|---|---|---|
| PP13,476 | P2 | 1/2003 | Bradford |
| PP15,809 | P2 | 6/2005 | Bradford |
| PP16,369 | P2 | 3/2006 | Bradford |

*Primary Examiner*—Annette H Para
*Assistant Examiner*—S. B. McCormick-Ewoldt

(57) ABSTRACT

The present invention relates to an interspecific tree and more particularly to a new and distinct variety broadly characterized by a medium size, vigorous, hardy, and productive tree. The present variety has a heavy bloom during the mid season, is self-unfruitful, and must be cross pollinated by a mid seasonal blooming apricot, plum or other interspecific tree. The fruit matures under the ecological conditions described during late June, with first picking on Jun. 23, 2007, and will hang on the tree for about fifteen more days. The fruit is uniformly medium in size, mostly red with greenish yellow mottling in skin color, clingstone in type, globose in shape, full red in flesh color, very firm and crisp in texture, and excellent in flavor.

1 Drawing Sheet

Botanical classification: *Prunus* sp.
Varietal denomination: 'Plumsweet X'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumsweet X'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one tree of 'YUMMY®gem' (U.S. Plant Pat. No. 15,809) plum was crossed by me in this manner. To pollinate this isolated tree, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H10P881". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'YUMMY® gem' (U.S. Plant Pat. No. 15,809) plum by being self-unfruitful and producing fruit that is sweet and excellent in flavor, but is quite distinguished therefrom by producing fruit that is larger in size, that is mottled in skin color, that matures about twenty-five days later, and that is full red in flesh color instead of yellow.

The present variety is more similar to 'YUMMY® rosa' (U.S. Plant Pat. No. 13,476) plum by being self-unfruitful and by producing fruit that is medium in size, that is clingstone in type, that is globose in shape, and that matures in late June, but is distinguished therefrom by producing fruit that is firmer in texture, that is entirely red in flesh color, and that is dark red with greenish yellow mottling in skin color.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the mid season. The present variety's abundance of blossoms and pollen entices strong bee activity to facilitate pollination. The fruit matures under the ecological conditions described during late June, with first picking on Jun. 23, 2007, and will hang on the tree for about fifteen more days. The fruit is uniformly medium in size, mostly red with greenish yellow mottling in skin color, clingstone in type, globose in shape, full red in flesh color, very firm and crisp in texture, and excellent in flavor.

DRAWING

The accompanying photograph consists of four whole fruits positioned to display the characteristics of the skin color and form, two half fruits divided to reveal the flesh and stone, typical leaves, and an inset depicting the flower blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 5, 2007, on the original tree during its sixth growing season. The flower and bud descriptions were developed during the previous blooming season. All major color code designations are by reference to the Inter-Society Color Council, National Bureau of Standards. Common color names are also used occasionally.

PARENTAGE

Seed parent: 'YUMMY® GEM' plum (U.S. Plant Pat. No. 15,809).

Pollen parent: Unknown.

TREE

Size: Medium, reaching and maintaining a height of 11' [3.35m.] and a spread of 9' [2.74 m.] after six growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming plum or interspecific, such as 'Plumsweet V' (U.S. Plant Pat. No. 16,369).

Bearing: Regular bearer, with no crop failures observed.

Trunk:

*Size.*—Large, reaching a maximum diameter of 4¾" [121 mm.] after the sixth growing season.

*Texture.*—Shaggy.

*Bark color.*—A Dark brown [59. d.Br] and Moderate brown [58. m.Br] variegation with Moderate yellowish brown [77. m.yBr] crevices present.

*Lenticels.*—Approximate Number Per Square Inch: 12. Color: Strong yellowish brown [74. s.yBr]. Average Size: ¼" [6.4 mm.]. Shape: Eye-shaped, elongated.

Branches:

*Size.*—Diameter of limb is 3" [76 mm] measured 12" above the crotch, 1⅜" [35 mm.] measured 12" above the first fork.

*Texture.*—Smooth on first and second year wood, increasing roughness with age.

*Color.*—1st Year Wood Topside: Moderate yellowish brown [77. m.yBr]. 1st Year Wood Underside: Brilliant yellow green [116. brill.YG]. Older Wood: A Dark grayish brown [62. d.gy.Br] and Dark brown [59. d.Br] variegation.

*Lenticels.*—Number Per Square Inch: More than 50 on second year wood. Color: Light grayish yellowish brown [79. l.gy.yBr]. Average Size: 1/32" [0.8 mm.]. Shape: Rectangular, elongated.

Leaves:

*Size.*—Large. Average Length: 3 9/16" [91 mm.]. Average Width: 1¾" [45 mm.].

*Arrangement.*—Alternate.

*Thickness.*—Medium.

*Form.*—Elliptical.

*Apex.*—Acuminate.

*Base.*—Some rounded, some acute.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.]. Color: Moderate reddish brown [43. m.rBr] topside, Light yellow green [119. l.YG] underneath.

*Stipules.*—Number: 2 per leaf, up to 6 per growing tip. Average Length: ¼" [6.4 mm.]. Color: Brilliant yellow green [116. brill.YG] becoming Moderate reddish brown [43. m.rBr] with age.

*Glands.*—Number: Mostly 2 per leaf. Position: Alternately positioned at the intersection of the petiole and the leaf blade. Size: Medium. Form: Globose. Color: Very yellow green [115. v.YG] becoming Deep reddish brown [41. deep rBr] in the center with age. Leaf buds: Pointed, medium.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Tip color.*—White [263. White].

Flowers: Perfect, complete, perigynous, usually a single pistil, typically thirty or more stamens, five sepals and petal locations alternately positioned.

*Average flower diameter.*—1 1/16" [27.0 mm.].

*Number of petals.*—Five, no double blossoms observed.

*Petal shape.*—Oval to circular.

*Petal margin.*—Entire, smooth to somewhat wavy.

*Average petal diameter.*—½" [12.7 mm.].

*Average petal length.*—9/16" [14.3 mm.].

*Petal apex.*—Rounded.

*Petal base.*—Obtuse.

*Petal color.*—White [263. White] on both sides.

*Anther color.*—Brilliant yellow [83. brill.Y].

*Stigma color.*—Light greenish yellow [101. l.gY].

*Sepal color.*—Brilliant yellow green [116. brill.YG] with a minor Grayish pink [8. gy.Pk] tinge on some.

*Sepal length.*—3/16" [4.8 mm.].
*Sepal width.*—5/32" [4.0 mm.].
*Sepal apex.*—Rounded to elliptical to match the width and length.
*Sepal margin.*—Fairly smooth to the naked eye, slightly serrate when magnified.
*Average pistil length.*—½" [12.7 mm.], some blanks observed.
*Average stamen length.*—½" [12.7 mm.].
*Fragrance.*—Moderate.
*Pollen production.*—Moderate.
*Blooming period.*—Medium, two days before 'Santa Rosa' plum (unpatented).
*Onset of bloom.*—One percent on Feb. 26, 2007.
*Date of full bloom.*—Mar. 4, 2007.
*Duration of bloom.*—One to two weeks, dependent on ambient temperature.
*Bloom density.*—Heavy.
*Number per cluster.*—2 to 10, average 4.

FRUIT

Maturity when described: Firm ripe, Jul. 5, 2007.
Date of first picking: Jun. 23, 2007.
Date of last picking: Jul. 7, 2007.
Size: Uniform, Medium.
*Average diameter axially.*—2 7/16" [61.9 mm.].
*Average diameter across cheek plane.*—2 7/16" [61.9 mm.].
*Average diameter across suture plane.*—2 7/16" [61.9 mm.].
*Typical weight.*—5.3 ounces [150 grams].
Form: Uniform, globose, symmetrical.
*Longitudinal section form.*—Round.
*Transverse section through diameter.*—Round.
Suture: A distinct line located in a very shallow groove extending from the base to the apex.
Ventral surface: Rounded, slightly lipped toward the base.
Lips: Fairly equal.
Cavity: Flaring, rounded, suture showing on one side.
*Depth.*—¼" [6.4 mm.].
*Breadth.*—11/16" [17.5 mm.].
Base: Truncate, slightly cordate if viewed parallel to the suture.
Apex: Rounded.
Pistil point: An inconspicuous dot.
Stem: Medium.
*Average length.*—7/16" [11.1 mm.].
*Average width.*—5/64" [2.0 mm.].
Skin:
*Thickness.*—Medium.
*Surface.*—Smooth.
*Tenacity.*—Tenacious to the flesh.
*Astringency.*—Moderate.
*Tendency to crack.*—None observed in dry season.
*Color.*—Very dark red [17. v.d.R] and Dark greenish yellow [103. d.gY] mottling over a Moderate red [15. m.R] background with Light grayish olive [109. l.gy.Ol] freckling throughout.
*Bloom.*—Abundant.
Flesh:
*Color.*—Deep red [13. deep R] with Very deep red [14. v.deep R] streaking next to the skin and stone.
*Surface of pit cavity.*—Covered with Very deep red [14. v.deep R] broken fibers when twisted from the stone.
*Amygdalin.*—Moderate.
*Juice.*—Abundant, rich.
*Texture.*—Firm, crisp.
*Fibers.*—Abundant, fine, tender.
*Ripens.*—Slightly earlier toward the apex.
*Flavor.*—A tasty blend of acid and sugar, typically 18–20 brix.
*Aroma.*—Moderate.
*Eating quality.*—Excellent.

STONE

Type: Clingstone.
Form: Oval.
Hilum: Narrow, oblong.
Base: Straight.
Apex: Mucronate, with a sharp 1/16" [1.6 mm.] tip.
Sides: Equal.
Surface: Rough throughout with one groove from base to apex on each side of the dorsal fin.
External color of stone: Deep yellowish brown [75. deep yBr].
Pit wall color when cracked: Dark orange yellow [72. d.OY].
Cavity surface color: Strong yellowish brown [74. s.yBr].
Average pit wall thickness: 1/16" [1.6 mm.].
Average width: 11/16" [17.5 mm.].
Average length: 13/16" [20.6 mm.].
Average breadth: 5/16" [7.9 mm.].
Tendency to split: None observed.
Kernel:
*Form.*—Oval.
*Skin color.*—Strong yellowish brown [74. s.yBr] when dry.
*Pellicle color.*—Deep yellowish brown [75. deep yBr].
*Vein color.*—Deep yellowish brown [75. deep yBr].
*Taste.*—Bitter.
*Viable.*—Yes.
*Average width.*—⅜" [9.5 mm.].
*Average length.*—½" [12.7 mm.].
*Amygdalin.*—Moderate.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'YUMMY® rosa' (U.S. Plant Pat. No. 13,476) plum by being self-unfruitful and by producing fruit that is medium in size, that is clingstone in type, that is globose in shape, and that matures in late June, but is distinguished therefrom by producing fruit that is firmer in texture, that is entirely red in flesh color, and that is dark red with greenish yellow mottling in skin color.

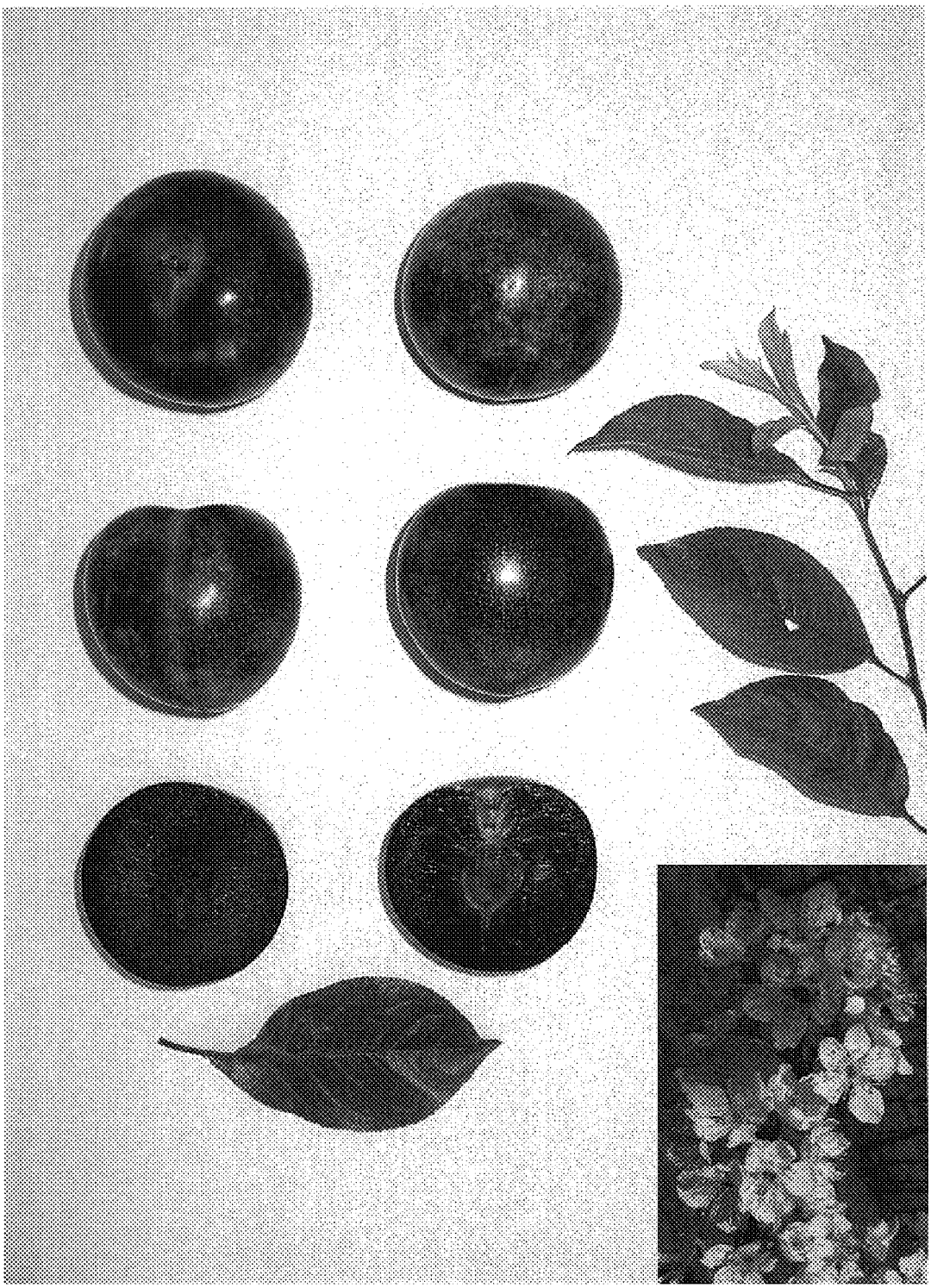

* * * * *